US00PP29028P2

(12) United States Plant Patent
Sato

(10) Patent No.: US PP29,028 P2
(45) Date of Patent: Feb. 27, 2018

(54) ***BIDENS* PLANT NAMED 'SUNBIDEVB 1'**

(50) Latin Name: *Bidens ferulifolia*
Varietal Denomination: Sunbidevb 1

(71) Applicant: Kazunori Sato, Tokyo (JP)

(72) Inventor: Kazunori Sato, Tokyo (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 15/330,325

(22) Filed: Sep. 6, 2016

(51) Int. Cl.
*A01H 5/02* (2006.01)

(52) U.S. Cl.
USPC ..... Plt./410

(58) Field of Classification Search
USPC ..... Plt./410
See application file for complete search history.

(56) References Cited

PUBLICATIONS

UPOV hit on bidens plant named 'Sunbidevb 1', JP PBR 30833, filed Feb. 17, 2016.*

* cited by examiner

*Primary Examiner* — Anne M Grunberg
(74) *Attorney, Agent, or Firm* — C. A. Whealy

(57) ABSTRACT

A new and distinct cultivar of *Bidens* plant named 'Sunbidevb 1', characterized by its upright to outwardly spreading and mounding plant habit; moderate vigorous growth habit; freely branching habit; freely flowering habit; year-round flowering habit; inflorescences with bright yellow-colored ray florets which become lighter yellow towards the apex under high temperatures conditions; and good garden performance.

1 Drawing Sheet

Botanical designation: *Bidens ferulifolia.*
Cultivar denomination: 'SUNBIDEVB 1'.

BACKGROUND OF THE INVENTION

The present invention relates to a new and distinct cultivar of *Bidens* plant, botanically known as *Bidens ferulifolia* and hereinafter referred to by the name 'Sunbidevb 1'.

The new *Bidens* plant is a product of a planned breeding program conducted by the Inventor in Fukaya, Saitama, Japan. The objective of the breeding program is to create new compact and mounding *Bidens* plants with year-round flowering habit and numerous attractive inflorescences.

The new *Bidens* plant originated from a cross-pollination made by the Inventor in Fukaya, Saitama, Japan during the spring of 2010 of two unnamed proprietary selections of *Bidens ferulifolia*, not patented. The new *Bidens* plant was discovered and selected by the Inventor as a single flowering plant from within the progeny of the stated cross-pollination in a controlled greenhouse environment in Fukaya, Saitama, Japan during the autumn of 2010.

Asexual reproduction of the new *Bidens* plant by vegetative cuttings in a controlled environment in Fukaya, Saitama, Japan since the spring of 2011 has shown that the unique features of this new *Bidens* plant are stable and reproduced true to type in successive generations.

SUMMARY OF THE INVENTION

Plants of the new *Bidens* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sunbidevb 1'. These characteristics in combination distinguish 'Sunbidevb 1' as a new and distinct *Bidens* plant:

1. Upright to outwardly spreading and mounding plant habit.
2. Moderate vigorous growth habit.
3. Freely branching habit.
4. Freely flowering habit.
5. Year-round flowering habit.
6. Inflorescences with bright yellow-colored ray florets which become lighter yellow towards the apex under high temperatures conditions.
7. Good garden performance.

Plants of the new *Bidens* differ primarily from plants of the female parent selection in the following characteristics:

1. Leaves of plants of the new *Bidens* have serrated margins whereas leaves of plants of the female parent selection have entire margins.
2. Plants of the new *Bidens* are freely flowering year-round whereas plants of the female parent selection are not freely flowering under low temperature conditions.

Plants of the new *Bidens* differ primarily from plants of the male parent selection in the following characteristics:

1. Leaves of plants of the new *Bidens* have serrated margins whereas leaves of plants of the male parent selection have entire margins.
2. Plants of the new *Bidens* are freely flowering year-round whereas plants of the male parent selection are not freely flowering under high temperature and long photoperiods/short nyctoperiod conditions.

Plants of the new *Bidens* can be compared to plants of *Bidens ferulifolia* 'Danyel9', disclosed in U.S. Plant Pat. No.

20,968. In side-by-side comparisons, plants of the new *Bidens* differ primarily from plants of 'Danyel9' in the following characteristics:

1. Plants of the new *Bidens* are broader than and not as upright as plants of 'Danyel9'.
2. Plants of the new *Bidens* have smaller leaves than plants of 'Danyel9'.
3. Leaves of plants of the new *Bidens* have serrated margins whereas leaves of plants of 'Danyel9' have entire margins.
4. Plants of the new *Bidens* flower earlier than plants of 'Danyel9',
5. Plants of the new *Bidens* are freely flowering year-round whereas plants of 'Danyel9' are not freely flowering during the summer.
6. Plants of the new *Bidens* have smaller inflorescences than plants of 'Danyel9'.
7. Plants of the new *Bidens* do not produce seeds whereas plants of 'Danyel9' produce seeds.

BRIEF DESCRIPTION OF THE PHOTOGRAPHS

The accompanying photographs illustrate the overall appearance of the new *Bidens* plant showing the colors as true as it is reasonably possible to obtain in colored reproductions of this type. Colors in the photographs may differ slightly from the color values cited in the detailed botanical description which accurately describe the colors of the new *Bidens* plant.

The photograph at the top of the sheet comprises a side perspective view of a typical flowering plant of 'Sunbidevb 1' grown in a container.

The photograph at the bottom of the sheet is a close-up view of a typical flowering plant of 'Sunbidevb 1'.

DETAILED BOTANICAL DESCRIPTION

The aforementioned photographs and following observations and measurements describe plants grown in 18-cm containers during the summer in an outdoor nursery in Higashiomi, Shiga, Japan and under cultural practices typical of commercial *Bidens* production. During the production of the plants, day temperatures ranged from 20° C. to 30° C. and night temperatures ranged from 10° C. to 20° C. Plants were three months old when the photographs and description were taken. In the following description, color references are made to The Royal Horticultural Society Colour Chart, 2007 Edition, except where general terms of ordinary dictionary significance are used.

Botanical classification: *Bidens ferulifolia* 'Sunbidevb 1'.

Parentage:

*Female parent*.—Unnamed proprietary selection of *Bidens ferulifolia*, not patented.

*Male parent*.—Unnamed proprietary selection of *Bidens ferulifolia*, not patented.

Propagation:

*Type*.—By vegetative cuttings.

*Time to initiate roots, summer*.—About seven days at temperatures ranging from 20° C. to 25° C.

*Time to initiate roots, winter*.—About ten days at temperatures ranging from 12° C. to 15° C.

*Time to produce a rooted young plant, summer*.—About ten days at temperatures ranging from 20° C. to 25° C.

*Time to produce a rooted young plant, winter*.—About two weeks at temperatures ranging from 12° C. to 15° C.

*Root description*.—Fibrous; typically white in color, actual color of the roots is dependent on substrate composition, water quality, fertilizers, substrate temperature and physiological age of roots.

*Rooting habit*.—Freely branching.

Plant description:

*Plant and growth habit*.—Upright to outwardly spreading and mounding plant habit; moderately vigorous growth habit.

*Branching habit*.—Freely branching habit with numerous primary and secondary lateral branches potentially forming at every node.

*Plant height*.—About 28 cm.

*Plant diameter or spread*.—About 62 cm.

*Lateral branches*.—Length: About 19 cm. Diameter: About 1.1 mm. Internode length: About 2.2 cm. Strength: Strong. Texture: Pubescent. Color: Close to 144B and tinged with close to N199A.

Leaf description:

*Arrangement*.—Opposite, simple.

*Length*.—About 2.1 cm.

*Width*.—About 1.7 cm.

*Shape*.—Roughly deltoid; pinnatisect.

*Apex*.—Acute.

*Base*.—Truncate.

*Margin*.—Serrate.

*Texture, upper and lower surfaces*.—Sparsely pubescent.

*Venation pattern*.—Pinnate, reticulate.

*Color*.—Developing and fully expanded leaves, upper surface: Close to 137C; venation, close to 137D. Developing and fully expanded leaves, lower surface: Close to 138C; venation, close to 138C.

*Petioles*.—Length: About 5.1 mm. Diameter: About 0.8 mm. Texture, upper and lower surfaces: Sparsely pubescent. Color, upper and lower surfaces: Close to 137D.

Inflorescence description:

*Appearance*.—Single (daisy) inflorescence form with ray and disc florets forming acropetally on a receptacle; inflorescences positioned above and beyond the foliar plane on strong peduncles; inflorescences face mostly upright.

*Flowering habit*.—Freely flowering habit with about 180 inflorescences developing per plant.

*Fragrance*.—None detected.

*Natural flowering season*.—Plants flower year-round in Japan; early flowering habit, plants begin flowering about four weeks after planting rooted young plants.

*Inflorescence longevity*.—Individual inflorescences last about seven to ten days on the plant; inflorescences not persistent.

*Inflorescence buds*.—Height: About 8.4 mm. Diameter: About 4.3 mm. Shape: Ovoid. Color: Close to 6A.

*Inflorescence size*.—Diameter: About 3.2 cm. Depth (height): About 7.5 mm. Disc diameter: About 7 mm.

*Receptacles*.—Diameter: About 5.5 mm. Height: About 0.9 mm. Color: Close to 145B.

*Ray florets*.—Number of ray florets per inflorescence: About six to eight arranged in a single whorl. Length: About 1.9 cm. Width: About 8.8 mm. Shape: Elliptic. Apex: Rounded and shallowly emarginate.

Base: Obtuse. Margin: Entire. Aspect: Horizontal to recurved. Texture, upper and lower surfaces: Smooth, glabrous. Color: When opening, upper surface: Close to 9A. When opening, lower surface: Close to 9B. Fully opened, upper surface: Close to 12A to 12B; color does not change with development; distally, under high temperatures conditions, color becomes closer to between 9D and 11D. Fully opened, lower surface: Close to 12A with stripes, close to N200A; under high temperatures conditions, color becomes closer to 9B.

*Disc florets*.—Number of disc florets per inflorescence: About 50. Shape: Tubular, elongated; apex, five-pointed. Length: About 5 mm. Diameter: About 1.5 mm. Texture, inner and outer surfaces: Smooth, glabrous. Color, when opening, inner and outer surfaces: Close to 13A. Color, fully opened, inner and outer surfaces: Close to 22A.

*Phyllaries*.—Quantity per inflorescence: About ten in a single whorl. Length: About 3.5 mm. Width: About 0.9 mm. Shape: Lanceolate. Apex: Acute. Base: Truncate, fused. Margin: Entire. Texture, upper and lower surfaces: Smooth, glabrous. Color, upper and lower surfaces: Close to 137C.

*Peduncles*.—Length, terminal peduncle: About 4.2 cm. Diameter: About 0.9 mm. Strength: Strong; flexible. Aspect: Upright to outwardly, inflorescences held above and beyond the foliar plane. Texture: Smooth, glabrous. Color: Close to 144B tinged with close to N199A.

*Reproductive organs*.—Androecium: Present on disc florets only. Quantity per disc floret: Five. Filament length: About 1.5 mm. Filament color: Close to 145C. Anther shape: Ellipsoidal. Anther length: About 1.3 mm. Anther color: Close to 165A. Pollen amount: Moderate. Pollen color: Close to 14A. Gynoecium: Present on ray and disc florets. Pistil length: About 5.1 mm. Style length: About 3.7 mm. Style color: Close to 8C. Stigma shape: Bifurcate; apex curled outwardly. Stigma color: Close to 21A. Ovary color: Close to 16D.

*Seeds*.—Seed development has not been observed on plants of the new *Bidens*.

Disease & pest resistance: Plants of the new *Bidens* have not been shown to be resistant to pathogens and pests common to *Bidens* plants.

Garden performance: Plants of the new *Clematis* have exhibited good garden performance and to tolerate rain, wind and temperatures ranging from 5° C. to 35° C.

It is claimed:

1. A new and distinct *Bidens* plant named 'Sunbidevb 1' as illustrated and described.

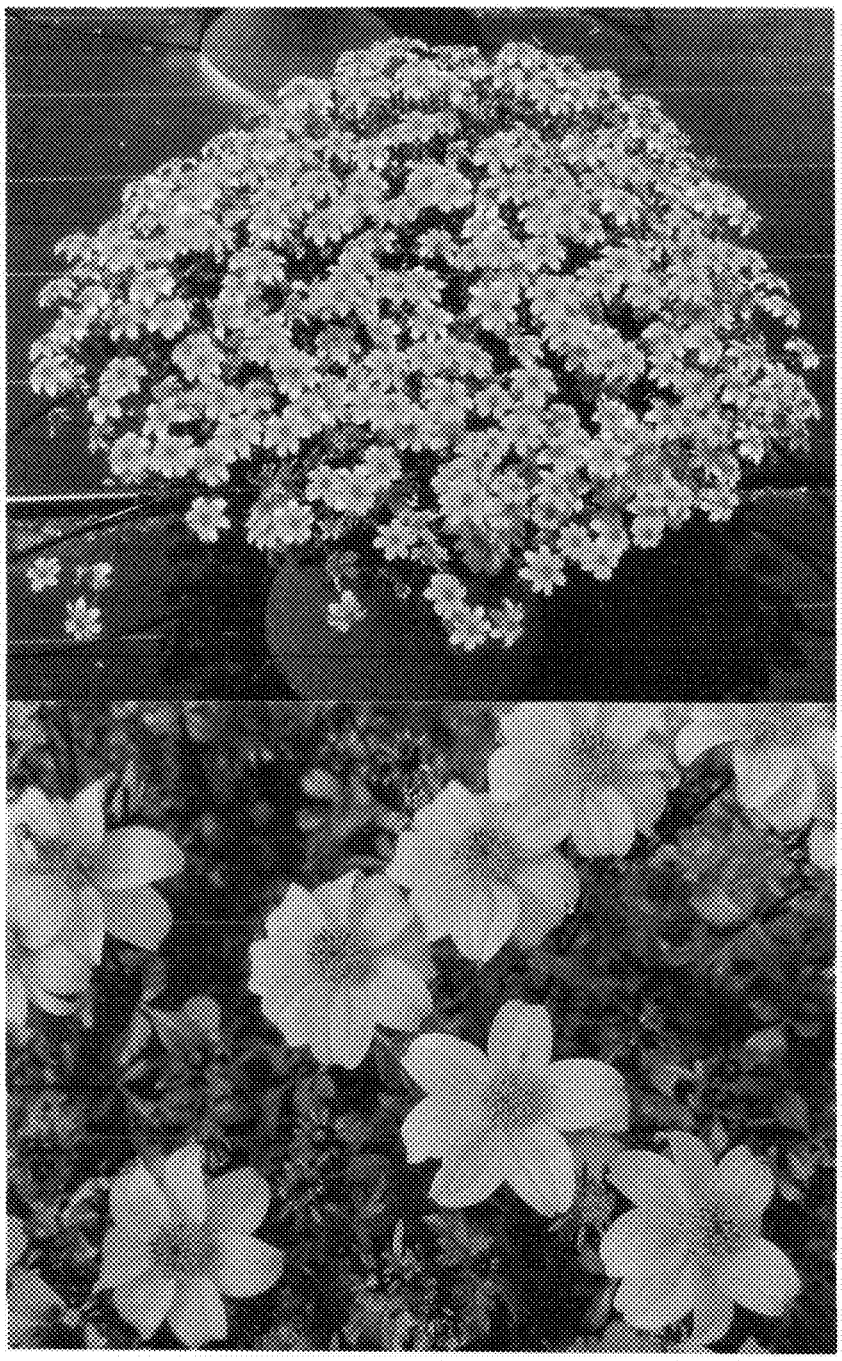

* * * * *